United States Patent [19]

Sofranko et al.

[11] Patent Number: 5,198,590

[45] Date of Patent: Mar. 30, 1993

[54] HYDROCARBON CONVERSION

[75] Inventors: John A. Sofranko; Glenn E Cozzone; John C. Jubin, Jr., all of West Chester; W. Wayne Wentzheimer, Glen Mills, all of Pa.

[73] Assignee: Arco Chemical Technology, L.P., Wilmington, Del.

[21] Appl. No.: 923,018

[22] Filed: Jul. 30, 1992

Related U.S. Application Data

[63] Continuation of Ser. No. 826,739, Jan. 28, 1992, abandoned.

[51] Int. Cl.$^5$ .............................................. C07C 41/66
[52] U.S. Cl. .................................... 568/697; 585/310; 585/653
[58] Field of Search ................. 568/697; 585/310, 653

[56] References Cited

U.S. PATENT DOCUMENTS

| | | |
|---|---|---|
| 3,748,251 | 7/1973 | Demmel et al. . |
| 3,849,291 | 11/1974 | Owen . |
| 3,894,931 | 7/1975 | Nace et al. . |
| 3,894,933 | 7/1975 | Owen et al. . |
| 3,894,934 | 7/1975 | Owen et al. . |
| 3,894,935 | 7/1975 | Owen et al. . |
| 3,926,778 | 12/1975 | Owen et al. . |
| 3,928,172 | 12/1975 | Davis, Jr. et al. . |
| 4,116,814 | 9/1978 | Zahner . |
| 4,500,651 | 2/1985 | Lok et al. . |
| 4,575,566 | 3/1986 | Vora . |
| 4,605,787 | 8/1986 | Chu et al. . |
| 4,606,810 | 8/1986 | Krambeck et al. . |
| 4,683,217 | 7/1987 | Lok et al. . |
| 4,758,419 | 7/1988 | Lok et al. . |
| 4,793,984 | 12/1988 | Lok et al. . |
| 4,814,519 | 3/1989 | Harandi et al. . |
| 4,826,507 | 5/1989 | Harandi et al. . |
| 4,827,043 | 5/1989 | Harandi et al. . |
| 4,830,635 | 5/1989 | Harandi et al. . |
| 4,835,329 | 5/1989 | Harandi et al. . |
| 4,854,939 | 8/1989 | Harandi et al. . |
| 4,857,667 | 8/1989 | Harandi et al. . |
| 4,882,038 | 11/1989 | Lok et al. . |
| 4,925,455 | 5/1990 | Harandi et al. . |
| 4,957,709 | 9/1990 | Harandi et al. . |
| 4,962,239 | 10/1990 | Bell et al. . |
| 4,966,680 | 10/1990 | Avidan et al. . |
| 4,966,681 | 10/1990 | Herbst et al. . |
| 4,967,020 | 10/1990 | Marler et al. . |
| 4,969,987 | 11/1990 | Le et al. . |
| 4,973,460 | 11/1990 | Flanigen et al. . |
| 4,973,785 | 11/1990 | Lok et al. . |
| 4,988,366 | 1/1991 | Harandi et al. . |
| 5,001,292 | 3/1991 | Harandi et al. . |
| 5,003,112 | 3/1991 | Knifton et al. . |
| 5,009,859 | 4/1991 | Harandi et al. . |
| 5,013,329 | 5/1991 | Bell et al. . |
| 5,015,782 | 5/1991 | Harandi et al. . |
| 5,049,360 | 9/1991 | Harandi et al. . |
| 5,100,533 | 3/1992 | Le et al. ............................ 568/697 |

FOREIGN PATENT DOCUMENTS 0026041  4/1981  European Pat. Off. .

Primary Examiner—Howard T. Mars
Attorney, Agent, or Firm—William C. Long

[57] ABSTRACT

Low value feed hydrocarbons are converted to high octane value tertiary ethers using a multiple riser fluidized solids catalytic reactor wherein in a first riser the hydrocarbon feed is converted to iso and linear $C_4$ and $C_5$ olefins, the iso-olefins are etherified, the linear $C_4$ and $C_5$ olefins are isomerized to iso $C_4$ and $C_5$ olefins in a second riser of the fluidized solids reactor, iso $C_4$ and $C_5$ olefins from the second riser are also etherified to high octane value tertiary ethers, and catalyst from both risers is regenerated in a common regeneration zone.

4 Claims, 1 Drawing Sheet

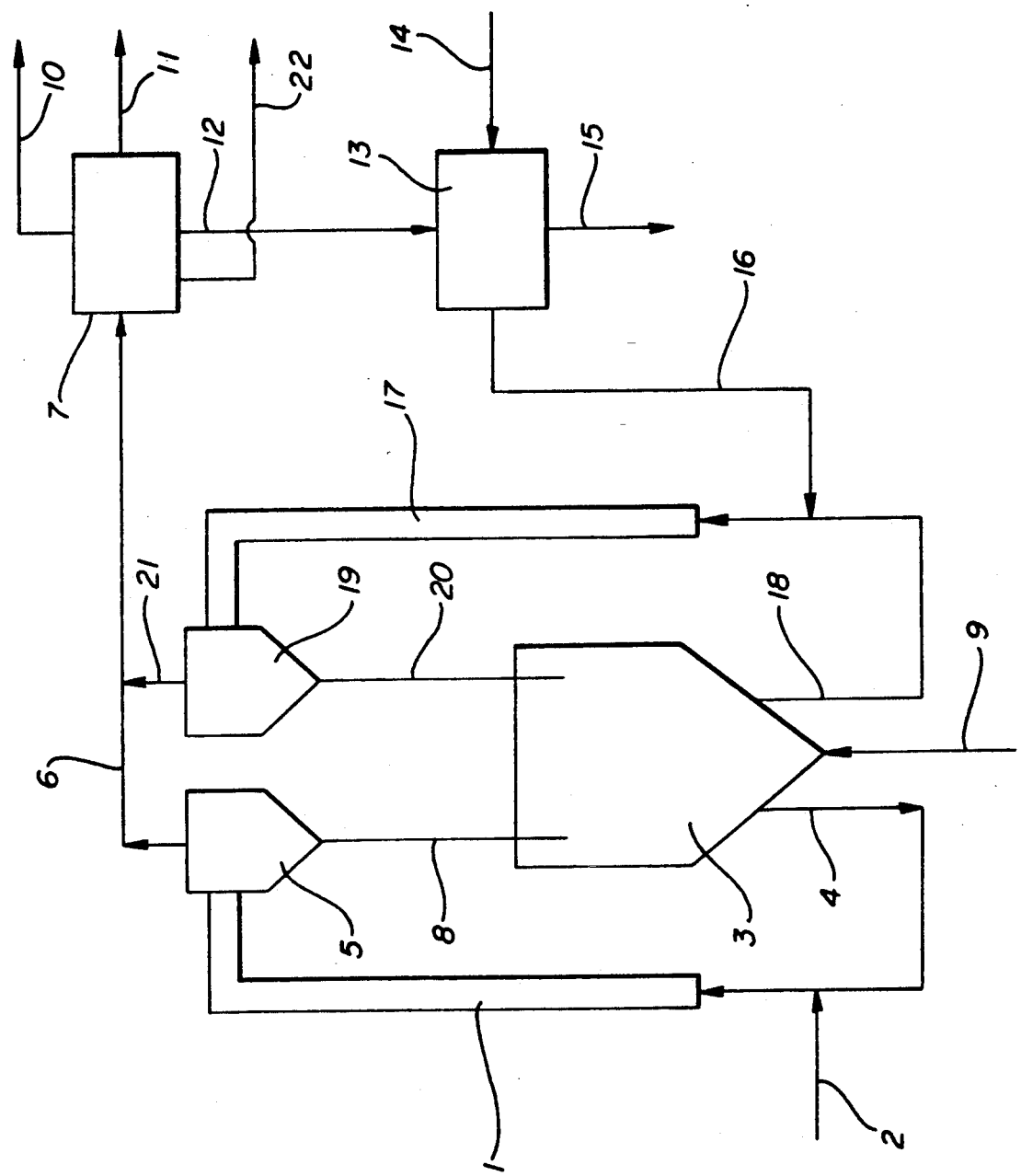

HYDROCARBON CONVERSION

This is a continuation of copending application Ser. No. 07/826,739 filed on Jan. 28, 1992, now abandoned.

BACKGROUND OF THE INVENTION

1. Field of the Invention

The present invention relates to fluidized solid catalytic conversions of hydrocarbons wherein a fluidized solids catalytic reactor is employed which has a plurality of risers and a common regeneration zone and wherein different reactions are carried out in the risers. In particular, the invention provides for the conversion of hydrocarbon streams which are of relatively low value to high value oxygenated fuels by a novel procedure which involves several catalytic conversion reactions using the same catalyst in separate risers in a fluidized solids catalytic reactor with a common regeneration zone in combination with an etherification reaction to convert iso-alkenes formed in one or both of the risers to high octane ethers such as methyl tertiary butyl ether (MTBE) and tertiary amyl methyl ether (TAME).

2. Description of the Prior Art

The use of fluidized solids catalytic reactors with multiple users is quite well known. Illustrative patents describing such operations include U.S. Pat. Nos. 4,966,681, 4,606,810, 3,748,251, 3,849,291, 3,894,931, 3,894,933, 3,894,934, 3,894,935, 3,926,778, 3,928,172, 3,974,062 and 4,116,814.

Various methods are known in the art for the conversion of branched olefins to the corresponding ether and/or alcohol. See U.S. Pat. Nos. 4,605,787, 4,575,566, 4,925,455, 4,957,709, 4,962,239, 4,967,020, 4,969,987, 4,830,685, 4,835,329, 4,827,045, 4,826,507, 4,814,519, 5,001,292, 5,003,112 and the like.

Likewise, methods are known whereby linear olefins can be converted by skeletal isomerization to branched olefins. See, for example, U.S. Pat. Nos. 4,037,029, 4,793,984, 4,683,217, 4,973,785, 4,882,038, 4,758,419, 4,500,651, 4,973,460 and the like.

Various integrated processes for the conversion of hydrocarbons to gasoline components which involve etherification of branched tertiary $C_4$ and/or $C_5$ olefins are also known. See, for example, U.S. Pat. Nos. 4,988,366, 4,925,455, 4,957,709, 4,969,987, 4,830,635, 4,835,329, 4,827,045, 4,826,507, 4,854,939, 5,001,292, 4,857,667, 5,009,859, 5,015,782, 5,013,329 and the like.

European publication 0 026,041 describes a process for producing olefins and/or ethers of high octane number from a wide $C_2$ to $C_{10}$ olefinic stream. The wide olefinic feedstock is restructured over a zeolite catalyst to form primarily $C_4$ to $C_7$ olefins, the $C_4$ to $C_7$ iso-olefins are reacted with methanol to form high octane ethers and unreacted olefins and methanol are separated from the ether product and recycled to the restructuring operation.

U.S. Pat. No. 4,814,519 shows a two-stage process for the production of ethers from olefin-containing feedstock such as from an FCC unit whereby the feedstock is reacted under conditions to maximize production of $C_4$-$C_5$ iso-olefins, particularly tertiary iso-olefins. The resulting iso-olefin rich product is then subjected to a catalytic etherification reaction to produce ethers such as TAME.

BRIEF DESCRIPTION OF THE INVENTION

In accordance with the invention, in a first fluidized solids catalytic reactor riser, a low value refinery hydrocarbon stream is catalytically reacted using a catalyst such as ZSM-5 to convert the low value hydrocarbons to a $C_4$ to $C_5$ olefins containing stream. The $C_4$ and $C_5$ olefins are separated from this product stream and then reacted in an etherification reaction, for example with methanol, to convert iso $C_4$ and $C_5$ olefins contained therein to the ether, e.g. MTBE and TAME. After ether separation, unreacted linear $C_4$ and $C_5$ olefins are catalytically reacted in a separate riser of the same fluidized solids catalytic reactor using the same catalyst, e.g. ZSM-5, at conditions which are different from those in the first riser effective to isomerize the linear $C_4$ to $C_5$ olefins to iso-olefins which are also etherified in the etherification zone above described. Deactivated catalyst from the various separate risers is regenerated in the common regeneration zone of the reactor.

DESCRIPTION OF THE DRAWING

Practice of the invention is illustrated schematically in the attached drawing.

DETAILED DESCRIPTION

The present invention makes use of the fact that different hydrocarbon conversion reactions can be accomplished with the same catalyst depending upon the feedstock and the reaction conditions. Basically, in a first fluidized solid catalyzed reaction a low value hydrocarbon feed material is converted to a $C_4$ and/or $C_5$ iso-olefins containing product stream.

Where the feedstock is a heavy paraffin and/or olefin fraction, the initial reaction is a cracking reaction which converts the heavy materials to the lighter, iso-olefins containing product fraction. Where the feedstock is a light olefins containing fraction, such as an ethylene and propylene fraction also containing methane, ethane and propane, the initial reaction is an oligomerization reaction which converts the light olefins to higher $C_4$ and $C_5$ olefins. Where both heavy and light feedstocks are available, both reactions can be carried out in the same riser, or each in a separate riser of a fluidized solids catalytic reactor.

The $C_4$ and $C_5$ olefins containing product from either or both of the above reactions is passed to an etherification zone wherein the iso $C_4$ and iso $C_5$ olefins are selectively reacted with an alcohol such as methanol to form MTBE and TAME.

Unreacted linear $C_4$ and $C_5$ olefins, after separation of MTBE and TAME, are passed to a separate reaction riser in the fluidized solids catalytic reactor and therein reacted with the same catalyst used in the fluidized solids catalytic reaction at conditions effective to structurally isomerize the linear $C_4$ and $C_5$ olefins to iso $C_4$ and iso $C_5$ olefin and the product stream containing these is returned for etherification in the above etherification zone.

Referring to the accompanying drawing, there is schematically depicted a dual riser fluidized solids catalyst reactor for use in carrying out the invention. The reactor consists of a first vertical riser 1 into which the low value hydrocarbon feed stream is fed via line 2. Catalyst particles from regeneration zone 3 pass via line 4 to riser 1; it is generally preferred to also pass a stripping gas such as steam to riser 1 to assist in the reaction (not shown). The admixture of feed gas, stripping gas and catalyst passes upwardly through riser 1 at hydrocarbon conversion conditions effective to convert the hydrocarbon feedstock to products including $C_4$ and $C_5$ iso-olefins.

The reaction mixture passes from riser 1 into cyclone separator 5 wherein separation of solids and gases takes place. Although depicted as a single cyclone separator, it will be apparent that in actual practice it is generally desired to employ a series of such separators. The gases pass from cyclone separator 5 via line 6 to separation zone 7. Spent catalyst passes from cyclone 5 via line 8 to regeneration zone 3 wherein the catalyst particles are regenerated by contact with an oxidizing gas such as air which is introduced via line 9.

The gaseous reaction mixture from cyclone 5 is separated in separation zone 7 by conventional distillation procedures into a plurality of separate fractions. A light stream comprised of $C_2$ and lighter materials is separated by means of line 10.

A propylene product stream is separated from zone 7 by means of line 11. A $C_4/C_5$ olefin stream is recovered and transferred by means of line 12 to etherification zone 13. In zone 13, the $C_4$ and $C_5$ iso-olefins are reacted with methanol which is introduced via line 14 in order to convert the iso-olefins to MTBE and TAME which materials are recovered via line 15.

Unreacted linear olefins are transferred from zone 13 via line 16 to vertical riser 17. Catalyst from regeneration zone 3 is transferred by means of line 18 to riser 17, and a stripping gas can also be introduced into riser 17 to assist in the fluidization and in the reaction (not shown).

The mixture of catalyst, stripping gas and linear olefins passes upwardly through riser 17 at structural isomerization conditions effective to convert the linear olefins to the corresponding iso-olefins. The mixture from riser 17 passe to cyclone separator 19 wherein the gases are separated from solid catalyst particles. As with cyclone 5, a plurality of cyclone separators in series can be employed to accomplish the separation. Spent catalyst particles pass from separator 19 by means of line 20 to regeneration zone 3 where the catalyst particles are regenerated.

The gaseous reaction mixture passes from separator 19 via line 21 wherein they are admixed in line 6 with the gas mixture from separator 5 and sent to separation zone 7. A gasoline hydrocarbon mixture is recovered from separation zone 7 by means of line 22.

A preferred catalyst which is employed in the present invention is that described in co-pending application Ser. No. 07/692,333 filed Apr. 26, 1991. The active catalyst component is phosphorus-containing ZSM-5 having a surface Si/Al ratio in the range 20-60. Preferably, the phosphorus is added to the formed ZSM-5 as by impregnating the ZSM-5 with a phosphorus compound in accordance with the procedures described, for example, in U.S. Pat. No. 3,972,832. Less preferably, the phosphorus compound can be added to the multicomponent mixture from which the catalyst is formed. The phosphorus compound is added in amount sufficient to provide a final ZSM-5 composition having 0.1-10 wt. % phosphorus, preferably 1-3 wt. %.

The phosphorus-containing ZSM-5 is preferably combined with known binders or matrices such as silica, kaolin, calcium bentonite, alumina, silica aluminate and the like. The ZSM-5 generally comprises 1-50 wt. % of the catalyst composition, preferably 5-30 wt. % and most preferably 10-25 wt. %.

The surface Si/Al ratio is 20-60. Most conveniently, this is achieved by regulation of the amounts of the components which are used in formulation of the zeolite in accordance with known procedures.

In general, the ZSM-5 is ordinarily ion exchanged with a desired cation to replace alkali metal present in the zeolite as prepared. The exchange treatment is such as to reduce the alkali metal content of the final catalyst to less than about 0.5 weight percent, and preferably less than about 0.1 weight percent. The preferred proton source is ammonium chloride as opposed to hydrochloric acid, sulfuric acid and nitric acid. Ion exchange is suitably accomplished by conventional contact of the zeolite with an aqueous solution of the proton source.

A further important feature is the activation of the ZSM-5 catalyst with steam after incorporation of phosphorus therein. The steam treatment is best carried out as a discrete step prior to use of the catalyst in hydrocarbon conversion. The preferred method is to heat the catalyst at 500° to 700° C., preferably 550° to 600° C., under 1 to 5 atmospheres, preferably 1.5 to 3 atmospheres steam for 1 to 48 hours, preferably 15 to 30 hours. An alternative method is to add about 1 to 50 mol. % steam to the hydrocarbon feed during hydrocarbon conversion. This method calls for a longer time to achieve activation of the catalyst and thus is not preferred.

Where the lower value feed hydrocarbon is a higher olefinic or paraffinic or mixed olefin and paraffin feed, the feed is contacted in riser 1 with the ZSM-5 catalyst at conditions effective to form lower olefins. Generally, paraffins, olefins and mixtures of paraffins and olefins having 3 to 20 carbon atoms, preferably 4 to 12 carbon atoms comprise suitable feed materials.

The feed mixture may also contain aromatics, naphthenes and inerts such as nitrogen, but the benzene content should not exceed 30 wt. % of the total feed. At benzene concentrations above 40 wt. %, alkylation becomes significant, and light olefin yields are reduced. The feed mixture may also contain steam in amount up to 30 mol. %, preferably 1 to 20 mol. %.

The hydrocarbon conversion is carried out at conditions which favor the formation of lower olefins. Reaction temperatures illustratively in the range 400° to 800° C. can be employed; the preferred temperature range being 500°-650 °C.

The hydrocarbon feed weight hourly space velocity (based on the ZSM-5 component of the catalyst) must be quite high in order to accomplish the efficient conversion to lower olefins. Weight hourly space velocities in the range 30-1000 hr.$^{-1}$, preferably 30-500 hr.$^{-1}$ and most preferably 40-100 hr.$^{-1}$ are suitable.

Low hydrocarbon partial pressures and low conversions per pass favor lower olefin production. The feed hydrocarbon can be admixed with steam or inert gas such as nitrogen. The hydrocarbon partial pressure is as low as practical, illustratively 10 to 30 psia. Where no diluents are employed, system pressures ranging from about −12 to 50 psig, preferably −5 to 30 psig, are suitable. Higher pressures can be used when diluents are employed.

High space velocity as above indicated and short residence times are preferred in order to maintain the desired low conversions per pass. Paraffin hydrocarbon conversions per pass are less than 50%. Reactor residence times illustratively are 0.1 to 20 seconds, preferably 1.0 to 5 seconds.

The conversion reaction of the instant invention is highly endothermic. Fluidized solid catalyst conversion procedures are used in riser 1 with the feed hydrocarbon vapor contacting fluidized particles of the zeolite catalyst. Heat necessary to maintain the reaction is provided by separately heating the catalyst particles in regeneration zone 3 as by combustion of appropriate fuel hydrocarbon.

Where the lower value feed hydrocarbon is a light hydrocarbon fraction, e.g. a $C_2$-$C_3$ mixture of olefins which may also contain $C_1$-$C_3$, the conditions of reaction in riser 1 are maintained to oligomerize the light olefins to $C_4$-$C_5$ olefins. The reaction conditions which are employed are essentially the same as those described above in connection with the conversion of the higher hydrocarbons to lower olefins.

The skeletal isomerization reaction in riser 17 is carried out in accordance with known procedures. Elevated temperatures of at least 450° C. and preferably 500° C. to about 600° C. are employed. Normal isomerization pressures ranging from about atmospheric to 100 psig are conveniently employed. Isomerization space velocities of the order of about 10 to 1000, preferably 100 to 200 hr.$^{-1}$ WHSV are useful.

The isomerization vapor feed can contain, in addition to the olefin to be isomerized, inert gas and/or steam.

The distillation separation in zone 7 is most conveniently carried out in a series of separate distillation zones by known procedures.

The etherification in zone 13 is likewise carried out by known means. Methanol is the preferred alkanol although lower alkanols having up to 4 carbon atoms can be used.

The reaction of lower alkanol such as methanol with iso $C_4$ and $C_5$ olefins at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149-152, discusses the technology. A preferred catalyst is a polymeric sulfonic acid exchange resin such as Amberlyst 15.

In the etherification process it is known that alkanol and iso-olefins may be reacted in equimolar quantities or either reactant may be in molar excess to influence the complete conversion of the other reactant. Because etherification is an incomplete reaction, the etherification effluent comprises unreacted alkanol and unreacted hydrocarbons. On a stoichiometric equivalencies basis, equimolar quantities of methanol and iso-olefins are advantageous, but an excess between 2 and 200% of either component can be passed to the etherification reaction unit. In the present invention, the molar ratio of alkanol to iso-olefin can be between 0.7 and 2.

The following example illustrates the invention.

Referring to the accompanying drawing and Table 1 herein, a pyrolysis gasoline fraction is fed via line 2 to riser 1 wherein it is contacted at reaction conditions effective to form lower olefins with steam activated ZSM-5 fluidized catalyst containing 2% by weight of phosphorous. Reaction conditions in riser 1 are 650° C. and 30 psig. WHSV is 40 hr.$^{-1}$.

Solid catalyst is separated from the reaction gas mixture in separator 5 and passes to separation zone 7 in combination with the reaction mixture from riser 17.

In separation zone 7 there are recovered by distillation a $C_2$ and lighter fraction which is recovered via line 10, a propylene fraction which is recovered via line 11, a gasoline fraction which is recovered via line 22, and a $C_4/C_5$ olefin fraction which is transferred via line 12 to etherification zone 13.

In zone 13, the iso $C_4$ and $C_5$ olefins are reacted in accordance with known procedures with methanol which is introduced via line 14. The reaction is carried out at 70° C. and 60 psig using a sulfonic acid ion exchange resin catalyst. Product MTBE and TAME are recovered via line 15.

Linear olefins are passed from zone 13 via line 16 to riser 17 wherein they are contacted with steam activated ZSM-5 containing 2% phosphorous from regeneration zone 3 via line 18. Reaction conditions in riser 17 are 593° C., 30 psig and a weight hourly space velocity of 100 hr.$^{-1}$.

The reaction mixture from riser 17 is separated in cyclone 19, the solid catalyst passing via line 20 to regeneration zone 3 and the reaction gases passing via line 21 to admixture with gases from riser 1 and then to separation zone 7.

Spent catalyst from zones 5 and 19 pass to zone 3 by lines 8 and 20 respectively, and in zone 3 the catalyst is regenerated by contact with air which is introduced via line 8.

The flow rates of the various streams and the content of the various components is given in the following Table 1.

TABLE 1

| | Flow Rate, M lbs./hr. | | | | | | | |
|---|---|---|---|---|---|---|---|---|
| | STREAM | | | | | | | |
| COMPONENT | 2 | 6 | 16 | 21 | 10 | 11 | 22 | 15 |
| Hydrogen | — | 0.28 | — | 0.18 | 0.47 | — | — | |
| Methane | — | 3.87 | — | 2.95 | 6.82 | — | — | |
| $C_2$= | — | 18.42 | — | 8.29 | 26.70 | — | — | |
| $C_2$ | — | 3.24 | — | 1.75 | 4.99 | — | — | |
| $C_3$= | — | 52.74 | — | 22.30 | — | 75.04 | — | |
| $C_3$ | — | 6.85 | — | 4.05 | — | 10.89 | — | |
| iso $C_4$= | — | 14.65 | — | 6.62 | — | — | — | 21.28* |
| n $C_4$= | — | 27.26 | 39.55 | 12.30 | — | — | — | |
| $C_4$ | — | 8.50 | 84.97 | 76.47 | — | — | — | |
| BD | — | — | 0.27 | 0.27 | — | — | — | |
| $C_5$= | 31.30 | 17.89 | 13.12 | 8.34 | — | — | — | 13.12* |
| $C_5$ | 31.30 | 19.30 | 81.42 | 62.12 | — | — | — | |
| $C_6$-$C_8$= | 98.00 | 12.96 | — | 6.03 | — | — | 19.00 | |
| $C_6$-$C_8$ | 77.00 | 36.96 | — | — | — | — | 36.96 | |
| aromatics | 147.10 | 158.98 | — | 6.01 | — | — | 164.99 | |
| $C_9$+ | 28.00 | 30.72 | — | 1.38 | — | — | 32.10 | |
| coke | — | 0.10 | — | 0.28 | — | — | — | |

TABLE 1-continued

| | Flow Rate, M lbs./hr. | | | | | | | |
|---|---|---|---|---|---|---|---|---|
| | STREAM | | | | | | | |
| COMPONENT | 2 | 6 | 16 | 21 | 10 | 11 | 22 | 15 |
| TOTAL | 412.70 | 412.74 | 214.34 | 219.34 | 38.98 | 85.93 | 253.05 | 34.39* |

*olefin equivalent which is converted to the methyl ether

We claim:

1. The process for the production of high octane value alkyl tertiary ethers from low value hydrocarbon feed which comprises reacting the low value feed in a first vertical riser of a fluidized solids catalytic reactor in contact with a fluidized solids catalyst at conditions effective to form iso $C_4$ and $C_5$ olefins as well as linear $C_4$ and $C_5$ olefins from said feed, separating gaseous products of the reaction including iso and linear $C_4$ and $C_5$ olefins from the catalyst, etherifying the iso $C_4$ and $C_5$ olefins and recovering product high octane value ethers, passing unreacted linear $C_4$ and $C_5$ olefins from the etherification to a second riser of said fluidized solid catalytic reactor, reacting the linear olefins in said second riser with said fluidized solids catalyst at conditions effective to structurally isomerize the linear $C_4$ and $C_5$ olefins to iso $C_4$ and $C_5$ olefins, separating the iso $C_4$ and $C_5$ olefins formed in the second riser from the fluidized solids catalyst, etherifying the iso $C_4$ and $C_5$ olefins to form high octane value tertiary alkyl ethers, passing spent catalyst from the first and second risers to a regeneration zone and regenerating the said spent catalyst.

2. The process of claim 1 wherein said low value hydrocarbon feed is a $C_3$-$C_{20}$ hydrocarbon feed.

3. The process of claim 1 wherein said low value hydrocarbon feed is a $C_1$-$C_3$ hydrocarbon feed.

4. The process of claim 1 wherein the iso $C_4$ and $C_5$ olefins are etherified by reaction with methanol.

* * * * *